(12) United States Patent
Ryan et al.

(10) Patent No.: US 6,251,440 B1
(45) Date of Patent: Jun. 26, 2001

(54) PESTICIDAL COMPOSITION

(75) Inventors: Robert Eugene Ryan; Sandra Morris, both of Norfolk (GB)

(73) Assignee: Barrier Biotech Limited, Norfolk (GB)

( * ) Notice: Subject to any disclaimer, the term of this patent is extended or adjusted under 35 U.S.C. 154(b) by 0 days.

(21) Appl. No.: 09/508,537

(22) PCT Filed: Oct. 9, 1998

(86) PCT No.: PCT/GB98/03039

§ 371 Date: Jun. 29, 2000

§ 102(e) Date: Jun. 29, 2000

(87) PCT Pub. No.: WO99/18802

PCT Pub. Date: Apr. 22, 1999

(30) Foreign Application Priority Data

Oct. 9, 1997 (GB) .................................................. 9721466

(51) Int. Cl.$^7$ .......................... A61K 35/75; A01N 25/00; A01N 25/08
(52) U.S. Cl. ............................ 424/742; 424/405; 424/409
(58) Field of Search ................................ 424/195.1, 405, 424/409, 742

(56) References Cited

U.S. PATENT DOCUMENTS

| | | | | |
|---|---|---|---|---|
| 4,587,123 | * | 5/1986 | Price | 424/195.1 |
| 5,645,845 | * | 7/1997 | Neumann et al. | 424/405 |
| 5,902,595 | * | 5/1999 | Burklow et al. | 424/405 |
| 5,911,915 | * | 6/1999 | Fonsny et al. | 252/312 |

FOREIGN PATENT DOCUMENTS

| | | |
|---|---|---|
| 0 629 345 | 12/1994 | (EP) . |
| 1467419 | * 3/1977 | (GB) . |
| WO 96 28033 | 9/1996 | (WO) . |

OTHER PUBLICATIONS

Chemical Abstracts, Oct. 13, 1986, Ahmed, S.M. et al., "Vapor toxicity and repellency of some essential oils to insects pests", XP002089702.

* cited by examiner

Primary Examiner—Christopher R. Tate
(74) Attorney, Agent, or Firm—Bacon & Thomas

(57) ABSTRACT

There is disclosed a pesticidal composition comprising by volume, approximately 40 to 60% eucalyptus oil, 10 to 30% cajaput oil, 10 to 30% lemongrass oils and 4 to 20% of surfactant. The composition is used in a method for controlling pesticidal activity at a locus which comprises applying an effective amount of the composition thereto.

12 Claims, No Drawings

PESTICIDAL COMPOSITION

The present invention is concerned with a pesticidal composition, and in particular with a pesticidal composition which may be used as an insecticide and/or a larvicide against, for example, ectoparasites, a major component of said composition comprising natural or essential oils.

Insects and their larvae are common pests of households, animals, crops, meat and poultry houses and the like. Typically, to eradicate such insect pests synthetically produced chemical pesticides are used. These compounds are generally highly toxic to mammals and plants and are often very slow to degrade making them unsuitable for wide spread application.

Examples of compounds which have previously been used for eradicating insects and their larvae include organophosphates which, although generally not as toxic as synthetic non-organsphosphates, still exhibit relatively high toxicity levels. They are, however, of limited use against some pests. For example, the larvae of the poultry house beetle are notoriously difficult to kill and are relatively unaffected by such organophosphates.

Essential oils have been used previously for use as pesticides. U.S. Pat. No. 4,587,123 discloses that eucalyptus oil is applied as a pesticide in a composition which includes a low molecular weight carbon content alcohol miscible with water. GB 1467 419 also discloses the use of eucalyptus oil as an insecticide in admixture with an extract of pepper. The compositions disclosed in these documents generally do not possess broad spectrum insecticidal or larvicidal activity.

Accordingly, it is an object of the present invention to provide a pesticidal composition which has broad spectrum activity and which is relatively non-toxic to mammals, particularly humans, or plants.

Therefore, there is provided by the present invention a pesticidal composition comprising by volume approximately 40 to 60% eucalyptus oil, 10 to 30% cajeput oil, 10 to 30% lemongrass oils and 4 to 20% of a surfactant. Preferably, the composition is further diluted with water, in which case the composition preferably comprises approximately 20 to 30% eucalyptus oil, 5 to 15% cajeput oil, 5 to 15% lemongrass oils, 40 to 60% water, and from 2% to 10% of a surfactant.

The inventors have surprisingly found that the composition according to the invention has a broad spectrum of activity and is particularly effective against insects having a cuticle or proteinaceous exoskeleton or the like. The presence of the surfactant is believed to confer the broad spectrum pesticidal activity on the composition. The surfactant functions as a penetrating agent which facilitates or aids penetration of the natural oils through the exoskeleton thus permitting the oils to exert their insecticidal activity on the internal organs and/or central nervous system of the insect or larva. Furthermore, the composition according to the present invention, comprises natural or essential oils as a major component and is therefore particularly advantageous in terms of its relative non-toxicity.

The composition is, advantageously, particularly active against poultry house beetle and its larvae. Poultry house beetle is a pernicious pest that is not readily destroyed by insecticidal agents even synthetic pesticides.

Preferably the composition comprises approximately, 25% eucalyptus oil, 10% cajeput oil, 10% lemongrass oils, 5% anionic surfactant and 50% water, which percentage values may deviate by plus or minus 10% for the respective ingredient.

As is known, oil of eucalyptus is obtained from various species of eucalyptus and the resulting oils do not possess a uniform analysis. It is believed, however, that the properties of the eucalyptus oil according to the invention are not dependent on a particular source of oil of eucalyptus and one may use oil derived from *Eucalyptus globulous* and *Eucalyptus dives*. Eucalyptus oil is rich in cineole and desirably eucalyptus oil according to the invention comprises cineole and preferably 1–8 cineole in an amount of from approximately 35 to 90% by volume.

Preferably, the surfactant may be an anionic surfactant and which may be selected from any one of the following; alkylarylsulfonates, alkanesulfonates, alcohol and alcohol ether sulfates, polyether carboxylates, olefinsulfonates, œ-sulfomonocarboxylic esters and phosphorous—containing anionic surfactants such as phosphoric acid, phosphorous acid, phosphonic acid and phosphinic acid derivatives. Preferably, the surfactant comprises sodium-2-ethylhexyl sulfosuccinate, and preferably in an amount greater than approximately 50%, optionally together with ethanol in an amount from approximately 10 to 25% by volume.

The composition according to the invention, may advantageously, be provided in the form of an oil based solution which provides for better foaming and gripping onto surfaces. Alternatively, the composition according to the invention may be formulated for spray application or as an aerosol. Alternatively the composition may be provided as a powder suitable for sprinkling or as a gel. In another embodiment of the invention, the composition may further include an appropriate attractant, such as a pheromone or the like, so as to attract the insect to the pesticidal composition.

If desired, the composition according to the invention may contain, or be applied in association with other insecticides or pesticides.

In another aspect of the present invention there is provided a method for controlling pesticidal activity at a locus, which method comprises applying thereto an effective amount of a composition according to the invention.

The present invention may be more clearly understood with reference to the following exemplary embodiment of the invention, which is given by way of example only.

Eucalyptus oil, cajeput oil, lemongrass oils, surfactant and water were suitably mixed in the percentage values of 25%, 10%, 10%, 5% and 50% by volume respectively, and subsequently diluted to 1 part per 50 parts water. The prepared solution was either sprayed directly onto the area of application or is provided in the form of a gel, or as a powder for sprinkling.

In the present example, the composition according to the invention was applied to mealworm, locusts (*locusta migrratieria*), the West Indian cockroach and to poultry house litter beetle (*Alphitobius Diapernus*).

In all cases as can be seen from Table 1 application of the composition resulted in death of the insect within a time period of between 1 to 10 minutes following its application. The insects generally exhibited nervous twitching prior to death indicating an effect on its central nervous system. Omission of the surfactant from the composition resulted in markedly reduced insecticidal effects. Other variations in the composition, such as omission of one of the oils also resulted in reduced insecticidal activity. The composition was highly successful in exterminating poultry house beetle and its larvae which are notoriously difficult to destroy.

TABLE 1

Barrier B Composition

| Organism | No. Destroyed | Time Elapsed |
| --- | --- | --- |
| Mealworm | All | 3 minutes |
| Cockroach | All | 4 minutes |
| Locust | All | 5 minutes |
| Poultry House Beetle | All | 1 ½ minutes |
| Larvae of Poultry House Beetle | All | 1½ minutes |

Barrier B = 25% Eucalyptus oil, 10% cajeput oil, 10% Lemongrass oils, 5% Surfactant, 50% Water

What is claimed is:

1. A pesticidal composition comprising, by volume, approximately 20 to 30% eucalyptus oil comprising cineol in an amount between 35 to 90% by volume, 5 to 15% cajeput oil, 5 to 15% lemongrass oils, 2 to 10% surfactant and 40 to 60% water.

2. A composition according to claim 1 which composition comprises by volume approximately 25% eucalyptus oil, 10% cajeput oil, 10% lemongrass oils, 5% surfactant and 50% water.

3. A composition according to claim 1 wherein said composition is further diluted to 1 part composition per 50 parts water.

4. A composition according to claim 1 wherein said surfactant is an anionic surfactant.

5. A composition according to claim 4 wherein said anionic surfactant is selected from the group consisting of alkylarylsulphonates, alkanesulfonates, alcohol and alcohol ether sulfates, polyether carboxylates, olefinsulfonates, œ-sulfomonocarboxylic esters and phosphorous containing anionic surfactants.

6. A composition according to claim 5 wherein said surfactant comprises sodium-2-ethylhexyl solfosuccinate.

7. A composition according to claim 1 which composition is provided in the form of an oil based solution, a water based solution, a powder or a gel.

8. A composition according to claim 1 which further comprises a suitable insect attractant.

9. A composition according to claim 8 wherein said attractant is a pheromone.

10. A composition according to claim 1 for use against insects having a cuticle or proteinaceous exoskeleton or their larvae.

11. A composition according to claim 1 for use against poultry house beetle or its larvae.

12. A process for controlling pesticidal activity at a locus, which process comprises applying thereto, an effective amount of a composition according to claim 1.

* * * * *